United States Patent [19]

Serur

[11] 4,038,192

[45] * July 26, 1977

[54] DEVICE FOR EXCHANGE BETWEEN FLUIDS SUITABLE FOR TREATMENT OF BLOOD

[75] Inventor: Juan Ricardo Serur, Brookline, Mass.

[73] Assignee: International Biomedical Laboratories, Inc., Boston, Mass.

[*] Notice: The portion of the term of this patent subsequent to July 15, 1992, has been disclaimed.

[21] Appl. No.: 595,846

[22] Filed: July 14, 1975

Related U.S. Application Data

[63] Continuation-in-part of Ser. No. 421,420, Dec. 3, 1973, Pat. No. 3,894,954.

[51] Int. Cl.² .............................................. B01D 31/00
[52] U.S. Cl. .......................... 210/321 B; 23/258.5 M
[58] Field of Search .......................... 210/22, 321, 494; 23/258.5 M

[56] References Cited

U.S. PATENT DOCUMENTS

| | | | |
|---|---|---|---|
| 3,411,630 | 11/1968 | Alwall et al. | 210/321 K |
| 3,516,548 | 6/1970 | Alwall et al. | 210/321 K |
| 3,631,986 | 1/1972 | Sausse | 210/321 K |
| 3,894,954 | 7/1975 | Serur | 210/321 K |

Primary Examiner—Frank A. Spear, Jr.

[57] ABSTRACT

A device for exchange between fluids, shown especially adapted for exchange between blood and a treatment fluid. The device comprises a first set of fluid channels for blood and a second set of channels for a treatment fluid. Each channel of the first set is defined by a pair of panels of semi-permeable membrane which are supported along spaced-apart lines by supports. At least a portion of the channels of the second set are defined by a pair of membrane panels and a pair of the supports. Each set of channels is arranged into a plurality of layers, the layers alternating between channels of the first and second sets. The resulting three dimensional array of blood and treatment fluid paths enables strict channeling to ensure equal exposure and flow of all blood and treatment fluid while simultaneously achieving double exposure of the treatment fluid as it flows between layers of blood.

12 Claims, 4 Drawing Figures

DEVICE FOR EXCHANGE BETWEEN FLUIDS SUITABLE FOR TREATMENT OF BLOOD

This application is a continuation-in-part of my co-pending application Ser. No. 421,420, filed Dec. 3, 1973, entitled Treatment of Blood issuing as U.S. Pat. No. 3,894,954 on July 15, 1975.

This invention relates to devices for exchange between fluids and is particularly suitable for the treatment of blood (e.g., dialysis) in which blood flowing in paths defined by semi-permeable membrane walls is exposed to treatment fluid flowing on the other side of the membrane walls.

It is a principal object of the present invention to provide for low cost fluid exchange or dialysis or oxygenation of blood in a unit of small size without a sacrifice in efficiency.

To achieve these and other objects, according to the invention first fluid (hereafter sometimes referred to as blood) flow paths are provided as a three dimensional array of narrow, elongated adjacent channels each defined by a pair of opposed membrane panels supported at channel edges by linear support structure, second (hereafter sometimes referred to treatment) fluid paths extending through the array having opposite sides along their length exposed to panels of different channels of the array. Preferably the device includes at least one layer, preferably a three dimensional array of layers, of narrow, elongated treatment fluid channels extending parallel to the blood channels, the layers disposed between and exposed on both sides to layers of the blood channels, the blood and treatment fluid channels mutually constructed to produce substantially uniform flow conditions for all blood and for all treatment fluid. According to a further aspect of the invention a three dimensional array of parallel, elongated, aligned support members cooperate to define the alternating layers of blood channels and treatment fluid channels mentioned above. In this array pairs of edge-opposed support members engage or press together along lines respective pairs of membrane panels to define the edges of respective blood channels, and pairs of side-opposed support members cooperate with panels of side-opposed blood channels to define respective treatment fluid channels. Preferably the membranes are continuous sheets across full sets of the support members, and define panels for a corresponding large number of channels.

Preferably the support members comprise elongated ribs having oppositely directed parallel edge surfaces engaging membrane panels of layers of the first fluid blood channels, walls of the ribs between the respective edges preventing communication between adjacent second fluid channels, effectively constraining second fluid in the layer to flow uniformly between and be exposed to opposed layers of the first fluid or blood. Preferably these ribs terminate at each end at cross members, the cross members including internal passages communicating with the second fluid channels between the ribs, while cross members of successive sets of ribs cooperate to define passages communicating with first fluid channels.

The device is preferably provided in the form of a stack of subunits, each comprising support members joined by a frame, adjacent subunits in the stack separated by a pair of sheet-form membranes. In this case, preferably adjacent pairs of the subunits include aligned recesses extending cross-wise to the support members, defining means for delivering untreated blood to a first end of each blood channel and a passage extends through each subunit cross-wise to the support members defining means for delivering treatment fluid to the treatment fluid channels defined between the support members.

The invention also features a blood inlet arrangement which divides a supply of blood into parallel discrete smaller streams through respective blood channels whereby rapid, uniform flow conditions and treatment can be assured for the blood, preferably in combination with a treatment fluid inlet arrangement which causes treatment fluid to flow in series through flow paths in successive layers whereby each element of treatment fluid is employed to treat blood in numerous blood channels, in the manner that can enable gravity feed of the treatment fluid while requiring a minimum supply of the fluid. This is achieved by a header for each layer, blood headers being connected in parallel, treatment headers connected in series.

Other objects, features, and advantages of the invention will appear from the following description of a particular preferred embodiment taken together with the accompanying drawings in which.

Figure 1:
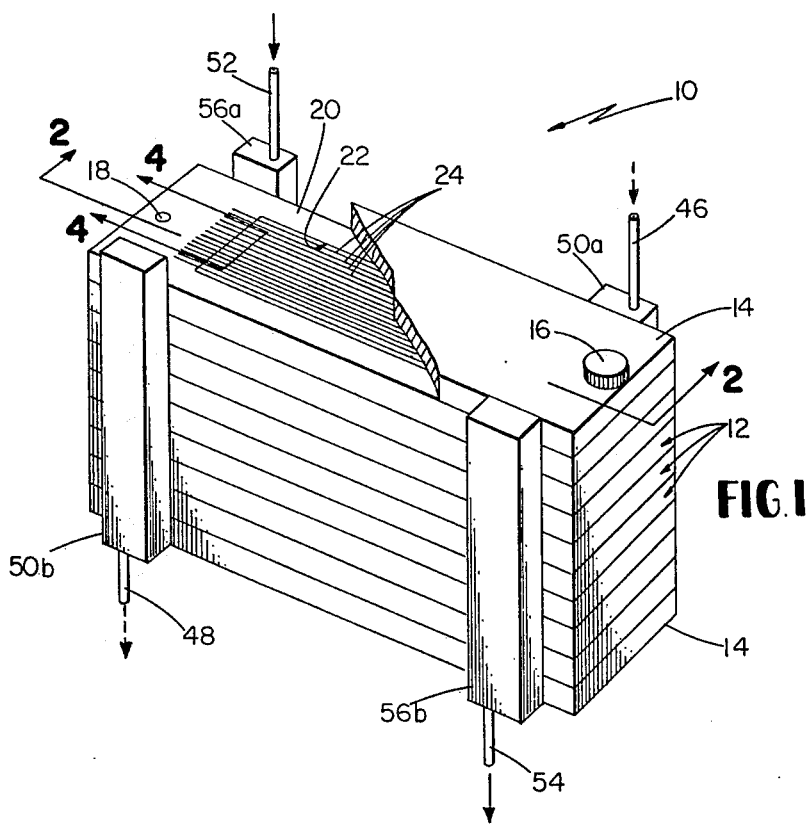
FIG. 1 is a partially broken away perspective view of a preferred embodiment of the present invention.

Referring to the drawings, according to the preferred embodiment, the device 10 is formed as a stack of identical subunits 12 with closure units 14 disposed at the top and bottom of the stack. This stack is retained as a unit, and rendered leakproof, by any conventional means such as bolts 16 which pass through openings 18 at opposite ends of each unit 12, 14 of the stack.

Figure 3:
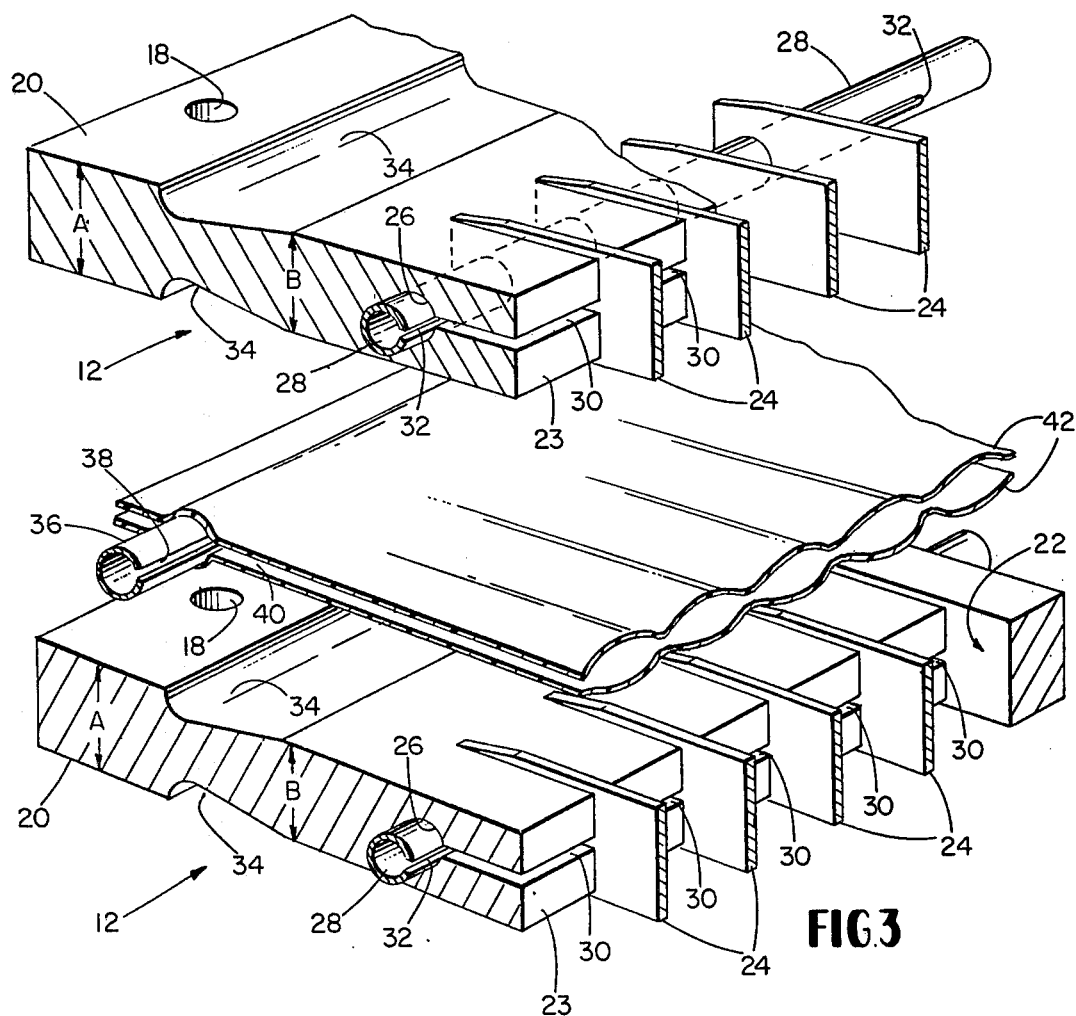
FIG. 3 is a partially broken away exploded view of a portion of the device of FIG. 1.

Each subunit 12 comprises a rectangular frame 20 having an open rectangular central portion 22. A plurality of longitudinally extending ribs 24 are mounted in the opening 22 in a parallel array. Ribs 24 can be formed from any material having sufficient rigidity (e.g., stainless steel, or molded of rigid plastic material) to achieve the support function of the ribs as discussed further below. In a typical device the ribs may be approximately 1 mm. thick and the same height as the maximum thickness of the subunit 20 (e.g., about 0.5 cm.) with a rib spacing of about 3 mm. The ribs 24 are mounted in the frame 20 at their longitudinal ends, which are fitted into appropriately sized vertical slots (see FIG. 3) in the longitudinal end walls 23 of the opening 22. A hole 26 extends through the frame 20, and the end portions of ribs 24, adjacent each end of the opening 22. A hollow tube 28, sized for a snug fit, is inserted into the hole 26. A horizontal slot 30 is cut in each end wall of opening 22 and communicates with the associated hole 26. The tube 28 has a longitudinal slot 32 which extends for the full width of the opening 22 and is aligned with the slot 30.

Figure 2:
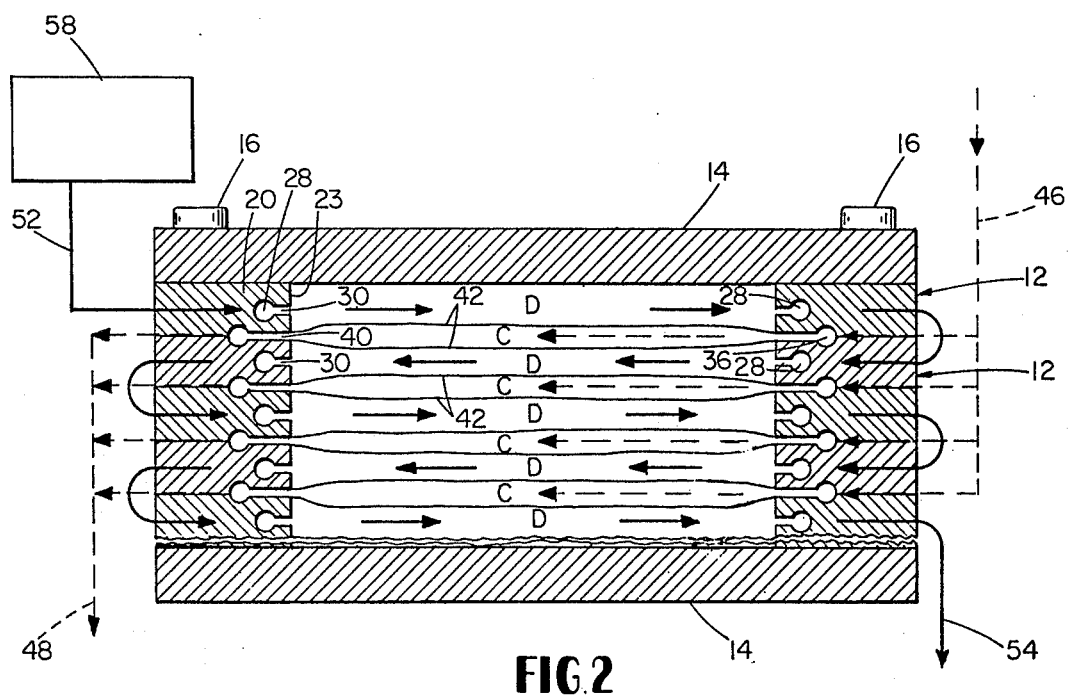
FIG. 2 is a somewhat schematic view taken at 2—2 of FIG. 1.

Recesses 34 extend across the width of the frame 20 on both the upper and lower surfaces thereof at each longitudinal end beyond the locations of holes 26. The recesses 34 of adjacent subunits 12 provide an opening for receiving a hollow tube 36 which extends for the full width of the frame 20 and which includes a horizontally disposed slot 38 which faces the opening 22 in the frame 20. The longitudinal ends of the frame 20 beyond the recesses 34 have a thickness A which is slightly greater than the thickness B of the frame on the other side of the recesses 34. As best seen in FIG. 2, this construction provides openings 40 in the stacked device between adjacent subunits 12, each opening being aligned with the associated slot 38 in a tube 36.

A double thickness of semi-permeable membrane 42 (e.g., cellophane) is disposed between each pair of adjacent subunits 12 and is of such size as to extend over the full width of the device 10 for the length of each frame 20 between the recesses 34 at opposite ends thereof. Each double thickness of membrane 42 extends between a pair of tubes 36, the slots 38 in those tubes communicating with the space between the two thicknesses of membrane 42.

Figure 4:
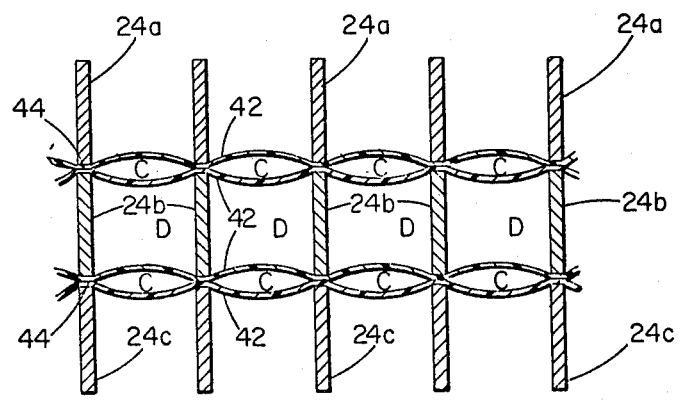
FIG. 4 is a somewhat schematic view taken at 4—4 of FIG. 1.

As best seen in FIG. 4, ribs of adjacent subunits 12 (e.g., ribs 24a, 24b) are vertically aligned with each other and are preferably, but not necessarily, sized to press togther the intervening double thickness of the membrane 42, as at 44, thereby forming a series of side-by-side blood channels C which have virtually 100% of their surface area formed from membrane 42. The ribs of any given subunit 12 (e.g., ribs 24b) also cooperate with the single thicknesses of membrane 42 immediately above and immediately below those ribs to define treatment fluid channels D. As is apparent from FIG. 4, each of the blood channels C is surrounded by treatment fluid in channels D above and below and each treatment fluid channel D (but for those adjacent the closure units 14) is simultaneously treating blood in two separate blood channels C.

Referring to FIGS. 1 and 2, blood (indicated by broken-line arrows) enters the device 10 through a conduit 46 and is removed from the device through a conduit 48. The conduits 46, 48 communicate with the internal channels (not shown) in units 50a, 50b which are disposed along the sides of the stack of subunits 12 and which provide communication with the various tubes 36. The unit 50a provides communication from the conduit 46 directly to each individual tube 36 so that, as best seen in FIG. 2, blood is delivered to the opening 40 associated with each tube 36 and then to each of the blood channels C simultaneously. The openings 40 assure a homogeneous pressure for the blood delivered to all channels C of the given layer. After the blood has passed the length of the membrane 42 from the tube 36 where it entered (i.e., at the right end of each subunit 12 as viewed in FIG. 1) to the remote tube 36 at that level, it is removed from the device by passages provided in the unit 50b which connect those tubes 36 with the conduit 48.

Treatment fluid (indicated in solid line arrows) enters the device 10 through a conduit 52 and is removed from the device through a conduit 54. Conduits 52 and 54 communicate with internal passages in units 56a, 56b which are symmetrically disposed with respect to units 50, discussed above. As best seen in FIG. 2, although schematically, the treatment fluid from a source 58 is delivered by conduit 52 only to the tube 28 at the left end of the first subunit 12. The treatment fluid flows the full length of the subunit 12 in its side-by-side channels D and then enters the tube 28 at the remote (i.e., right) end of the first subunit 12. The units 56 provide internal passages (not shown) which link the appropriate tubes 28 of adjacent subunits 12 so that the treatment fluid flows through the device in a serpentine fashion in the channels D of all subunits 12 before being removed from the last subunit 12 by the conduit 54.

As will be evident from the foregoing, and particularly from FIG. 4, the device 10 provides a large number of fluid channels, a first set of which (i.e., channels C) carry blood and a second set of which (i.e., channels D) carry treatment fluid. These channels are arranged in alternating layers of side-by-side channels so that each layer of channels C is sandwiched between two layers of channels D. Similarly, but for the uppermost and lowermost layers of channels D, each layer of channels D is in contact with a pair of layers of channels C across panels of membrane 42. With this arrangement in which each interior channel D services two blood channels C, it has been discovered that channels D can be of substantially smaller cross sectional area than heretofore thought possible.

Thus, for example, with a length of 40 cm. and width of 20 cm. for each opening 20 in a stack of five units 12 there will be adequate membrane 42 surface area for successful dialysis of human blood. With the present arrangement of each channel D treating two channels C, however, successful dialysis can be maintained in such a device even though the total cross sectional area of all channels D is reduced approximately 40% from the total such area of prior devices in which each channel D treated but one channel C. This, of course, leads to a substantial reduction in size of the device 10 and in the volume of treatment fluid required for each dialysis session with a patient.

While a particular prefered embodiment has been illustrated in the accompanying drawings and described in detail herein, other embodiments are within the scope of the invention and the following claims. As one example, it may be noted that the layers of channels need not be linear. While many configurations are undoubtedly feasible, the transversely "zig-zag" configuration disclosed in my prior U.S. Pat. No. 3,729,098, issued Apr. 24, 1973 may be particularly desirable.

What is claimed is:

1. In a device for treating blood comprising blood flow paths defined by semi-permeable membrane walls and treatment fluid paths exposing the blood to the treatment fluid across said membrane walls, the improvement wherein the blood flow paths comprise a three dimensional array of narrow, elongated adjacent channels each defined by a pair of opposed membrane panels supported at channel edges by linear support structure, and said treatment fluid paths extend through the array having opposite sides along their length defined by and exposed to panels of different blood channels of said array.

2. The device according to claim 1 wherein said treatment fluid paths include at least one layer of narrow, elongated channels extending parallel to said blood channels, said layer disposed between and exposed on both sides to layers of said blood channels, the blood and treatment fluid channels mutually constructed to produce substantially uniform flow conditions for all blood and for all treatment fluid.

3. The device according to claim 2 wherein a three-dimensional array of parallel, elongated, aligned support members cooperate to define said blood channels and treatment fluid channels, pairs of edge-opposed support members engaging respective pairs of membrane panels to define the edges of respective blood channels, and pairs of side-opposed support members cooperating with panels of side-opposed blood channels to define respective treatment fluid channels.

4. The device according to claim 3 in the form of a stack of subunits, each subunit comprising a plurality of said support members joined by a frame, adjacent subunits in said stack separated by two thicknesses of said membrane.

5. The device according to claim 4 wherein adjacent pairs of said subunits include aligned recesses extending cross-wise to said support members, defining means for delivering untreated blood to a first end of each blood channel.

6. The device according to claim 4 wherein a passage extends through each subunit cross-wise to said support members, defining means for delivering treatment fluid to the treatment fluid channels defined between said support members.

7. The device according to claim 2 wherein there are a plurality of layers of treatment fluid channels and a treatment fluid inlet arrangement is provided to cause treatment fluid to flow in series through flow paths in successive layers whereby each element of treatment fluid is employed to treat blood in numerous blood channels.

8. The device according to claim 1 wherein a blood inlet arrangement is provided to divide a supply of blood into parallel discrete smaller streams through respective blood channels whereby uniform flow conditions and treatment can be assured for the blood.

9. In a device for providing exchange between a first and second fluid comprising first fluid flow paths defined by semi-permeable membrane walls and second fluid paths exposed to the first fluid across said membrane walls, the improvement wherein the first fluid flow paths comprise a three dimensional array of narrow, elongated adjacent channels each defined by a pair of opposed membrane panels supported at channel edges by linear support structure, said second fluid paths extending through the array having opposite sides along their length exposed to panels of different first fluid channels of said array, said second fluid paths including at least one layer of narrow, elongated channels extending parallel to said first fluid channels, said layer disposed between and exposed on both sides to layers of said first fluid channels.

10. In a device for providing exchange between a first and second fluid comprising first fluid flow paths defined by semi-permeable membrane walls and second fluid paths exposed to the first fluid across said membrane walls, the improvement wherein the first fluid flow paths comprise a three dimensional array of narrow, elongated adjacent channels each defined by a pair of opposed membrane panels supported at channel edges by linear support structure, said second fluid paths extending through the array having opposite sides along their length exposed to panels of different first fluid channels of said array, said second fluid paths including at least one layer of narrow, elongated channels extending parallel to said first fluid channels, said layer disposed between and exposed on both sides to layers of said first fluid channels and wherein a three-dimensional array of parallel, elongated, aligned support members cooperate to define said first fluid and second fluid channels, pairs of edge-opposed support members engaging respective pairs of membrane panels to define the edges of respective first fluid channels, and pairs of side-opposed support members cooperating with panels of side-opposed first fluid channels to define respective second fluid channels.

11. The device of claim 10 wherein said support members defining said layer of second fluid channels comprise elongated ribs having oppositely directed parallel edge surfaces engaging membrane panels of layers of first fluid channels, walls of said ribs between the respective edges preventing communication between adjacent second fluid channels and effectively constraining second fluid in said layer to flow uniformly between and be exposed to opposed layers of said first fluid.

12. The device of claim 11 wherein said ribs terminate at each end at cross members, said cross members including internal passages communicating with the second fluid channels between said ribs, and cross members of successive sets of said ribs cooperating to define passages communicating with first fluid channels.

* * * * *